(12) United States Patent
Sano et al.

(10) Patent No.: US 9,433,359 B2
(45) Date of Patent: Sep. 6, 2016

(54) PIEZOELECTRIC PUMP AND BLOOD-PRESSURE INFORMATION MEASUREMENT DEVICE PROVIDED THEREWITH

(71) Applicant: OMRON HEALTHCARE CO., LTD., Muko-shi, Kyoto (JP)

(72) Inventors: Yoshihiko Sano, Kyoto (JP); Toshihiko Ogura, Kyoto (JP); Tatsuya Kobayashi, Kyoto (JP); Yuki Yamashita, Kyoto (JP); Yoshiki Doi, Kyoto (JP); Wataru Tsunoda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 14/404,829

(22) PCT Filed: Apr. 15, 2013

(86) PCT No.: PCT/JP2013/061188
§ 371 (c)(1),
(2) Date: Dec. 1, 2014

(87) PCT Pub. No.: WO2013/179789
PCT Pub. Date: Dec. 5, 2013

(65) Prior Publication Data
US 2015/0150470 A1    Jun. 4, 2015

(30) Foreign Application Priority Data

May 29, 2012 (JP) ................................. 2012-121794

(51) Int. Cl.
*A61B 5/022* (2006.01)
*A61B 5/0225* (2006.01)
(Continued)

(52) U.S. Cl.
CPC ......... *A61B 5/02233* (2013.01); *A61B 5/0225* (2013.01); *A61B 5/0235* (2013.01); *A61B 5/02141* (2013.01); *A61B 5/02225* (2013.01); *F04B 43/046* (2013.01)

(58) Field of Classification Search
CPC .. F04B 43/046; F04B 45/407; A61B 5/0235; A61B 5/02141
See application file for complete search history.

(56) References Cited

U.S. PATENT DOCUMENTS

| 4,587,974 A * | 5/1986 | Link .............................. 600/498 |
| 2009/0232683 A1* | 9/2009 | Hirata et al. ................ 417/413.2 |

(Continued)

FOREIGN PATENT DOCUMENTS

| JP | A-11-311184 | 11/1999 |
| JP | A-2007-198147 | 8/2007 |

(Continued)

OTHER PUBLICATIONS

Jul. 9, 2013 Search Report issued in International Patent Application No. PCT/JP2013/061188.

(Continued)

*Primary Examiner* — Patricia Mallari
*Assistant Examiner* — Michael Catina
(74) *Attorney, Agent, or Firm* — Oliff PLC (57) ABSTRACT

A piezoelectric pump is provided with an actuator containing a piezoelectric element and a vibrating sheet; a first diaphragm, positioned opposite the actuator, with a first connecting hole provided therein; a pump chamber formed by the space between the actuator and the first diaphragm; and a second diaphragm positioned opposite the first diaphragm. The part of the second diaphragm opposite the first connecting hole is provided with an opposing wall portion that prevents a fluid that has been introduced into the pump chamber via the first connecting hole from flowing back towards a suction side via the first connecting hole.

15 Claims, 9 Drawing Sheets

(51) Int. Cl.
*F04B 43/04* (2006.01)
*A61B 5/021* (2006.01)
*A61B 5/0235* (2006.01)

(56) References Cited

U.S. PATENT DOCUMENTS

2011/0079299 A1* 4/2011 Yuguchi et al. .............. 137/511
2012/0171062 A1* 7/2012 Kodama .............. F04B 43/046
417/413.2

FOREIGN PATENT DOCUMENTS

WO WO 2009/145064 A1 12/2009
WO WO 2011/145544 A1 11/2011

OTHER PUBLICATIONS

Jul. 9, 2013 Written Opinion issued in International Patent Application No. PCT/JP2013/061188.

* cited by examiner

PIEZOELECTRIC PUMP AND BLOOD-PRESSURE INFORMATION MEASUREMENT DEVICE PROVIDED THEREWITH

TECHNICAL FIELD

The present invention relates to a piezoelectric pump that suctions and discharges a fluid using a piezoelectric element and a blood pressure information measurement device including the piezoelectric pump as a pressure pump for pressurizing a compressing fluid bladder.

BACKGROUND ART

Measuring a subject's blood pressure information is extremely important in gaining an understanding of the subject's state of health. In recent years, attempts have been made to determine the cardiac stress or the level of arteriosclerosis not only by measuring a systolic blood pressure value and a diastolic blood pressure value, the usefulness of which as typical indices that contribute to the analysis of the risk of cardiovascular diseases such as stroke, heart failure, myocardial infarction, and the like has been widely acknowledged, but also, for example, by measuring the subject's pulse wave.

Blood pressure information measurement devices are intended to measure at least one of these types of blood pressure information, and are expected to be further used in fields such as early detection, prevention, and treatment of circulatory diseases. It should be noted that the blood pressure information includes a wide variety of types of circulatory information, such as systolic blood pressure values, diastolic blood pressure values, average blood pressure values, the pulse wave, the pulse, various indices indicating the level of arteriosclerosis, and the like.

Generally, a cuff for a blood pressure information measurement device (hereinafter also simply referred to as a "cuff") is used to measure blood pressure information. Here, a "cuff" means a band- or ring-shaped structure that contains a compressing fluid bladder that can be attached to a part of a living body, and refers to those for use in measurement of blood pressure information, where an artery is compressed by inflating the compressing fluid bladder by injecting a fluid, such as a gas, a liquid, or the like, into the aforementioned compressing fluid bladder.

Usually, a blood pressure information measurement device is provided with a pressurization pump and an exhaust valve, which serve as a pressurization/depressurization mechanism for increasing/reducing the pressure of the compressing fluid bladder. Of these components, the pressurization pump is intended to pressurize the compressing fluid bladder and conventionally, a motor pump has been generally used as the pressurization pump.

In recent years, however, small-sized piezoelectric pumps suitable for suctioning and discharging a compressible fluid, such as air and the like, have come into actual use, and the use of such a piezoelectric pump as the pressurization pump of a blood pressure information measurement device has been considered.

The aforementioned piezoelectric pumps come in various types of configuration. In one type, an actuator is constituted by attaching a piezoelectric element to a vibrating sheet, and a diaphragm having a connecting hole though which a fluid passes is positioned opposite the actuator. By resonantly driving the piezoelectric element to thereby vibrate the vibrating sheet, the space between the actuator and the diaphragm functions as a pump chamber for enabling a pumping operation.

In a piezoelectric pump with this configuration, a fluid is introduced into the pump chamber from the suction side via the aforementioned connecting hole by displacement of the actuator toward the side opposite to where the diaphragm is located, and subsequently, the fluid is delivered to the discharge side from the pump chamber by displacement of the actuator toward the side where the diaphragm is located.

It should be noted that documents disclosing piezoelectric pumps with this configuration include, for example, International Publication No. 2011/145544 (Patent Literature 1).

CITATION LIST

Patent Literature

Patent Literature 1: International Publication No. 2011/145544

SUMMARY OF INVENTION

Technical Problem

In a piezoelectric pump with the foregoing configuration, however, when the actuator is displaced toward the side where the diaphragm is located (i.e., when the pump chamber performs a discharging operation), part of the fluid in the pump chamber flows back (leaks) to the suction side via the connecting hole provided in the diaphragm. Because of this backflow of fluid, a piezoelectric pump with this configuration naturally has a limited pressurization capability.

Accordingly, if a piezoelectric pump with the foregoing configuration is used as the pressure pump of a blood pressure information measurement device, problems will arise, such as insufficient pressure force for pressurizing a compressing fluid bladder or a long time required to pressurize a compressing fluid bladder to a predetermined pressure, thus making it difficult to perform speedy measurement.

Accordingly, the present invention has been made to solve the foregoing problems, and the objects thereof are to provide a high-pressure, large-flow piezoelectric pump with a superior pressurization efficiency and also to provide a blood pressure information measurement device that, even if a piezoelectric pump is used as the pressure pump, does not generate insufficient pressure force for a compressing fluid bladder and is capable of performing speedy measurement.

Solution to Problem

A piezoelectric pump based on the present invention suctions a fluid from the outside and discharges the suctioned fluid to the outside, and the piezoelectric pump comprises: an actuator including a piezoelectric element and a vibrating sheet to which the piezoelectric element is attached, wherein the actuator is vibrated by the piezoelectric element being resonantly driven; a first diaphragm having therein a first connecting hole through which the fluid flows, wherein the first diaphragm is vibrated with the vibration of the actuator by being positioned opposite the actuator; a pump chamber formed by the space between the actuator and the first diaphragm, wherein the pump chamber introduces the fluid thereinto from a suction side via the first connecting hole by the actuator being displaced toward a side opposite to where the first diaphragm is located, and the pump chamber delivers the fluid to a discharge side by the actuator being displaced toward the side where the first diaphragm is located; and a backflow preventing portion for preventing the fluid introduced into the pump chamber via the first connecting hole from flowing back toward the suction side via the first connecting hole.

The piezoelectric pump based on the present invention preferably comprises a second diaphragm for being vibrated with the vibration of the first diaphragm by being on the opposite side of the first diaphragm from the actuator and positioned opposite the first diaphragm, and in that case, the backflow preventing portion is preferably composed of an opposing wall portion provided in a portion of the second diaphragm that opposes the first connecting hole.

In the piezoelectric pump based on the present invention, the second diaphragm is preferably composed of a component more difficult to deflect than the first diaphragm.

In the piezoelectric pump based on the present invention, preferably, a second connecting hole through which the fluid flows are provided in a surrounding portion outside of where the opposing wall portion of the second diaphragm is provided. In this case, the fluid is introduced into the pump chamber from the suction side via the second connecting hole and the first connecting hole by displacement of the actuator toward the opposite side to where the first diaphragm is located.

Preferably, the piezoelectric pump based on the present invention comprises a thin-film valve body attached to the portion of the first diaphragm facing the actuator in a manner that covers the first connecting hole, the valve body being capable of blocking or opening the first connecting hole, and in that case, the backflow preventing portion is preferably composed of the valve body.

In the piezoelectric pump based on the present invention, the valve body preferably functions as a check valve with part of the periphery thereof not joined to the first diaphragm.

In the piezoelectric pump based on the present invention, the valve body may also functions as a check valve by having a slit formed in a portion thereof.

A blood pressure information measurement device based on the present invention comprises the foregoing piezoelectric pump of the present invention as a pressure pump for pressurizing a compressing fluid bladder for compressing a living body.

Advantageous Effects of Invention

According to the present invention, a high-pressure, large-flow piezoelectric pump with a superior pressurization efficiency is provided, and also provided is a blood pressure information measurement device that, even if a piezoelectric pump is used as the pressure pump, does not generate insufficient pressure force for a compressing fluid bladder and is capable of performing speedy measurement.

DESCRIPTION OF EMBODIMENTS

Preferred embodiments of the present invention will be described hereinafter with reference to the drawings. In the following description of the embodiments, a so-called upper arm blood pressure monitor that can be used to measure a systolic blood pressure value and a diastolic blood pressure value of a subject by applying its cuff to the upper arm of the subject will be used as an example of a blood pressure information measurement device. It should be noted that in the embodiments described below, parts that are the same or common will be denoted by the same reference signs in the drawings, and descriptions thereof will not be repeated.

Embodiment 1

Figure 1:
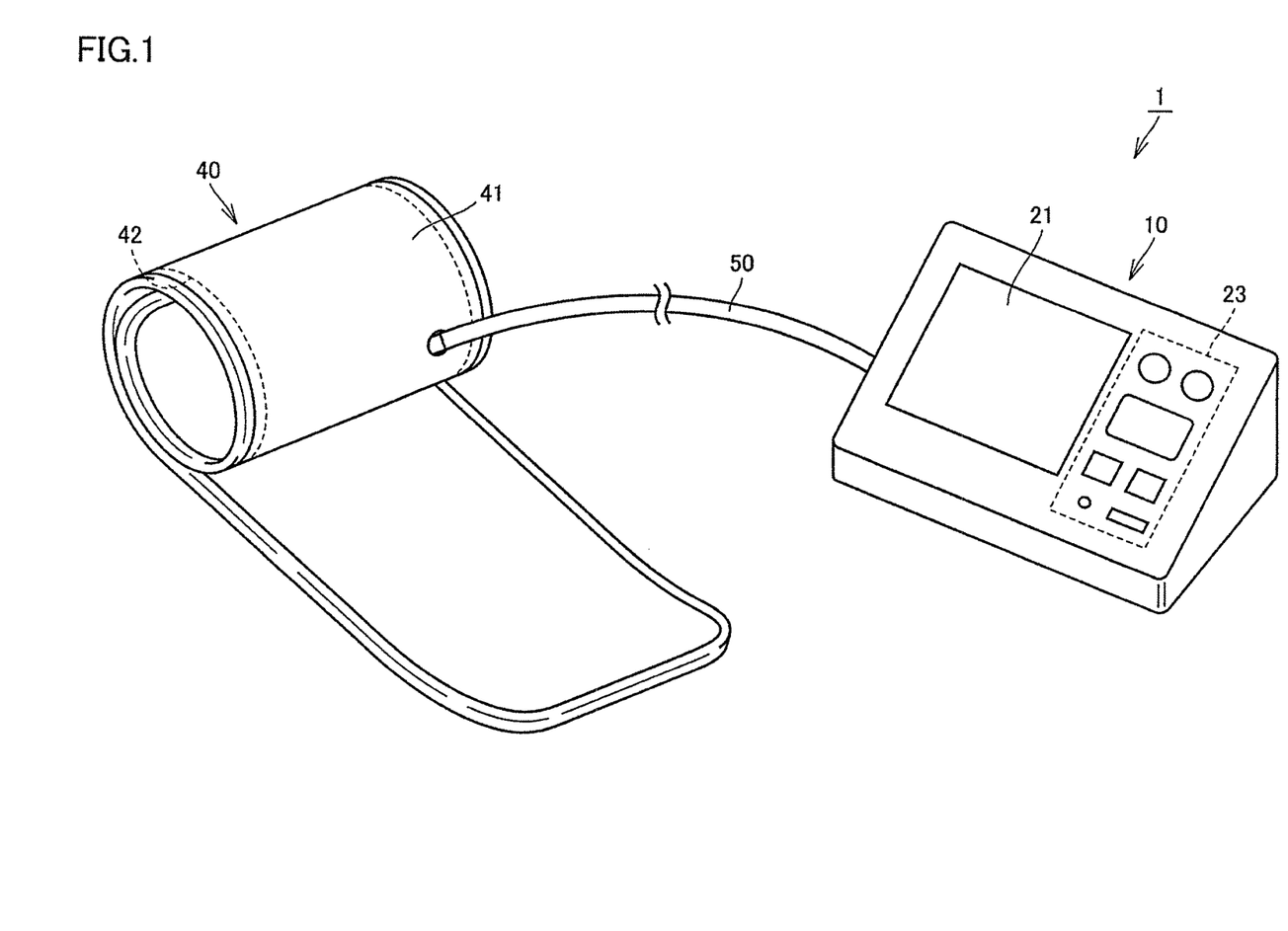
FIG. 1 is a perspective view showing an appearance of a blood pressure monitor of Embodiment 1 of the present invention.
Figure 2:
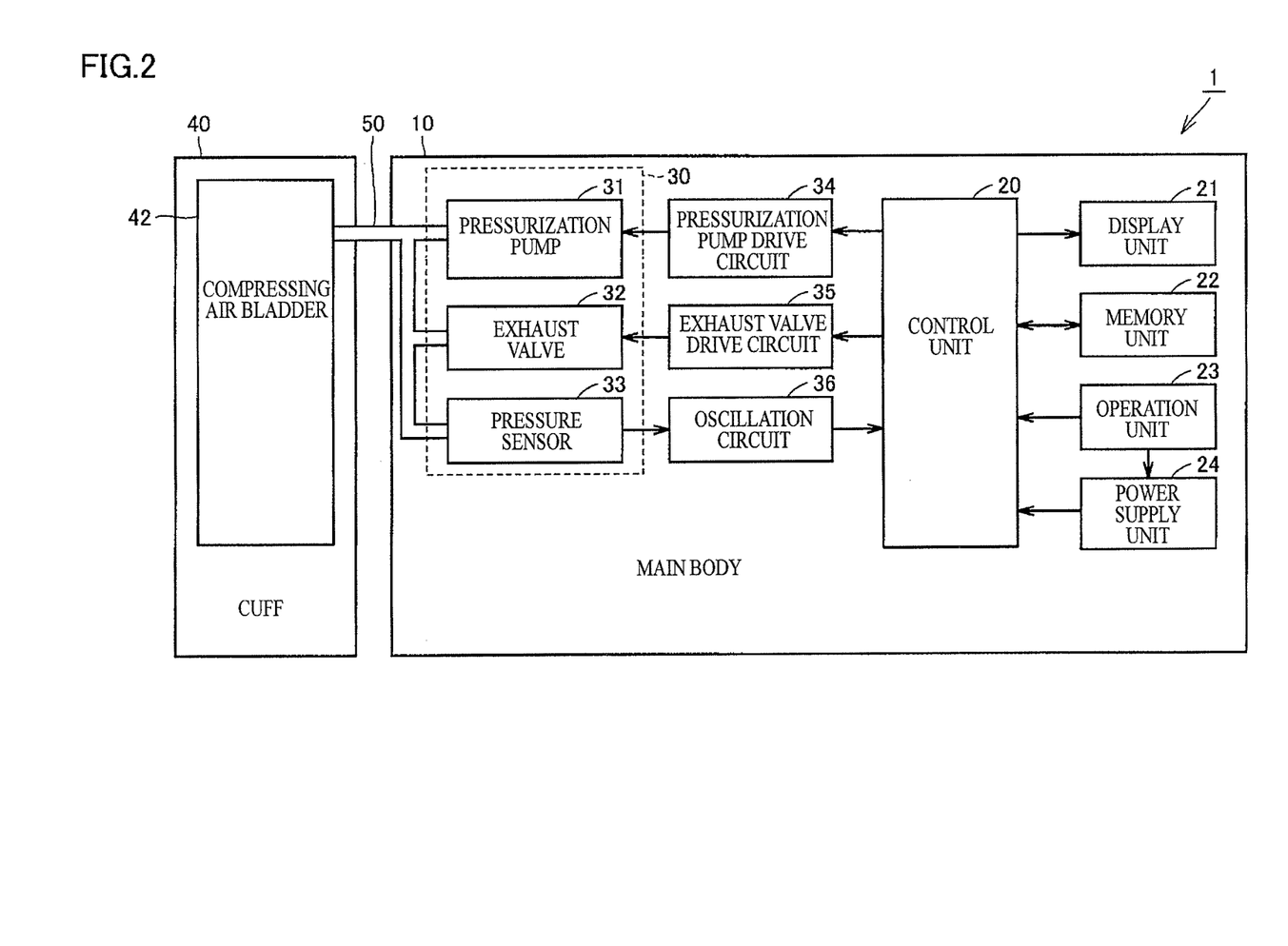
FIG. 2 is a diagram showing the configuration of functional blocks of the blood pressure monitor of Embodiment 1 of the present invention.

FIG. 1 is a perspective view showing an appearance of a blood pressure monitor of Embodiment 1 of the invention, and FIG. 2 is a diagram showing the configuration of functional blocks of the blood pressure monitor of the embodiment. With reference to FIGS. 1 and 2, the configuration of the blood pressure monitor 1 of this embodiment will be described first.

As shown in FIG. 1, the blood pressure monitor 1 of this embodiment includes a main body 10, a cuff 40, and an air tube 50. The main body 10 has a box-shaped case and has a display unit 21 and an operation unit 23 on an upper surface of the case. During measurement, the main body 10 is used while mounted on a mount surface such as a table. The cuff 40 has, as main components, a band- or bag-shaped outer package cover 41 and a compressing air bladder 42, which is a compressing fluid bladder, contained in the outer package cover 41, and has an approximately annular form as a whole. During measurement, the cuff 40 is used by being wrapped around an upper arm of the subject. The air tube 50 connects the main body 10 and the cuff 40 to each other, which are configured separately.

As shown in FIG. 2, the main body 10 has, in addition to the aforementioned display unit 21 and operation unit 23, a control unit 20, a memory unit 22, a power supply unit 24, a pressurization pump 31, an exhaust valve 32, a pressure sensor 33, a pressurization pump drive circuit 34, an exhaust valve drive circuit 35, and an oscillation circuit 36. The pressurization pump 31, the exhaust valve 32, and the pressure sensor 33 correspond to compressing air system components 30 that are provided in the blood pressure monitor 1, and in particular, the pressurization pump 31 and the exhaust valve 32 correspond to a pressurization/depressurization mechanism for increasing/reducing the internal pressure of the compressing air bladder 42.

The compressing air bladder 42 is intended to compress the upper arm when it is placed thereon, and has an inner space. The compressing air bladder 42 is connected via the aforementioned air tube 50 to each of the pressurization pump 31, the exhaust valve 32, and the pressure sensor 33, which are the aforementioned compressing air system components 30. Thus, the compressing air bladder 42 is pressurized and inflated by driving the pressurization pump 31, and the internal pressure of the compressing air bladder 42 is maintained or is reduced to deflate the compressing air bladder 42 by controlling the driving of the exhaust valve 32, which serves as a discharge valve.

The control unit 20 is composed of, for example, a CPU (Central Processing Unit) and is a means for performing overall control of the blood pressure monitor 1. The display unit 21 is composed of, for example, an LCD (Liquid Crystal Display) and is a means for displaying measurement results and the like. The memory unit 22 is composed of, for example, a ROM (Read-Only Memory) and a RAM (Random-Access Memory) and is a means for storing programs for causing the control unit 20 and the like to execute processing procedures for blood pressure measurement and storing measurement results and the like. The operation unit 23 is a means for accepting operations by the subject or the like and inputting the instructions from the outside to the control unit 20 and the power supply unit 24. The power supply unit 24 is a means for supplying electric power to the control unit 20.

The control unit 20 inputs control signals for driving the pressurization pump 31 and the exhaust valve 32 to the pressurization pump drive circuit 34 and the exhaust valve drive circuit 35, respectively, and inputs a blood pressure value, which is a measurement result, to the display unit 21 and the memory unit 22. Moreover, the control unit 20 includes a blood pressure information acquiring unit (not shown) that acquires a blood pressure value of the subject based on a pressure value detected by the pressure sensor 33. The blood pressure value acquired by this blood pressure information acquiring unit is then input to the aforementioned display unit 21 and memory unit 22 as a measurement result. It should be noted that the blood pressure monitor 1 may separately have an output unit that outputs a blood pressure value as a measurement result to an external device (e.g., a PC (Personal Computer), a printer, or the like). For example, a serial communication line, a writing device for writing to various types of recording media, and the like can be used as the output unit.

The pressurization pump drive circuit 34 controls the operation of the pressurization pump 31 based on the control signal input from the control unit 20. The exhaust valve drive circuit 35 controls the opening and closing operation of the exhaust valve 32 based on the control signal input from the control unit 20. The pressurization pump 31 is intended to increase the internal pressure (hereinafter also referred to as "cuff pressure") of the compressing air bladder 42 by supplying air into the interior of the compressing air bladder 42, and the operation thereof is controlled by the aforementioned pressurization pump drive circuit 34. The exhaust valve 32 is intended to maintain the internal pressure of the compressing air bladder 42 and to reduce the cuff pressure by opening the interior of the compressing air bladder 42 to the outside, and the operation thereof is controlled by the aforementioned exhaust valve drive circuit 35. The pressure sensor 33 detects the internal pressure of the compressing air bladder 42 and inputs an output signal corresponding to the detected internal pressure to the oscillation circuit 36. The oscillation circuit 36 generates a signal of an oscillation frequency corresponding to the capacitance of the pressure sensor 33 and inputs the generated signal to the control unit 20.

Figure 3:
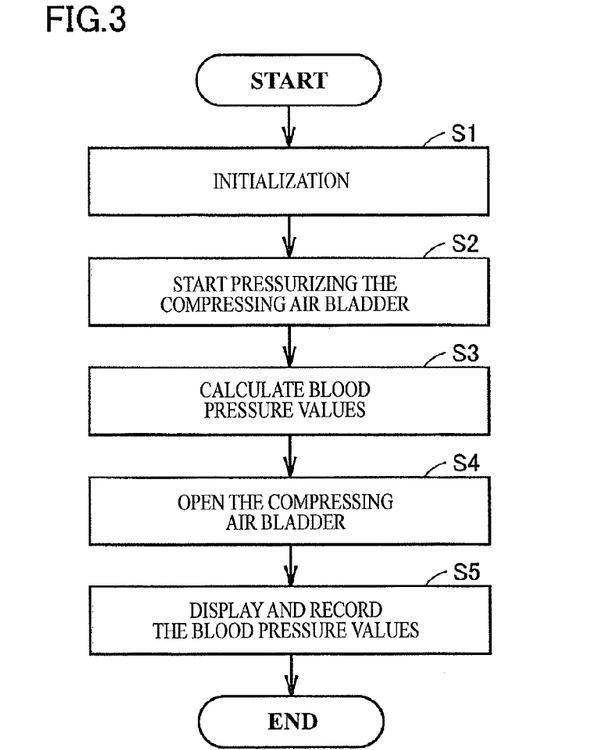
FIG. 3 is a diagram showing the operational flow of the blood pressure monitor of Embodiment 1 of the present invention.

FIG. 3 is a diagram showing the operational flow of the blood pressure monitor of this embodiment. Next, with reference to FIG. 3, the operational flow of the blood pressure monitor 1 of this embodiment will be described. It should be noted that a program conforming to the flow diagram illustrated in FIG. 3 is stored in the aforementioned memory unit 22 in advance, and processing thereof is performed by the control unit 20 reading out the program from the memory unit 22 and executing the program.

To measure a blood pressure value, the cuff 40 is attached to the subject in advance by being wrapped around an upper arm of the subject. In this state, when the power to the blood pressure monitor 1 is turned on by operating the operation unit 23 provided on the main body 10, electric power is supplied to the control unit 20 from the power supply unit 24 to activate the control unit 20. As illustrated in FIG. 3, after being activated, firstly, the control unit 20 initializes the blood pressure monitor 1 (step S1).

Then, the control unit 20 waits for an instruction to start measurement, and when an instruction to start measurement is input by operating the operation unit 23, the control unit 20 blocks the exhaust valve 32 and starts to drive the pressurization pump 31 to gradually increase the cuff pressure of the compressing air bladder 42 (step S2).

In the process of pressurization of the compressing air bladder 42, the control unit 20 calculates maximal and minimal blood pressure values using a known procedure (step S3). Specifically, in the process of increasing the cuff pressure of the compressing air bladder 42, the control unit 20 acquires the cuff pressure based on the oscillation frequency obtained from the oscillation circuit 36 and extracts pulse wave information, which is superimposed on the acquired cuff pressure. The control unit 20 then calculates the aforementioned blood pressure values based on the extracted pulse wave information.

Once the blood pressure values are calculated at step S3, the control unit 20 completely exhausts air in the compressing air bladder 42 by stopping the operation of the pressurization pump 31 and opening the exhaust valve 32 (step S4), and displays the blood pressure values as a measurement result on the display unit 21 while storing those blood pressure values in the memory unit 22 (step S5).

Subsequently, the control unit 20 terminates the operation after receiving an instruction to turn off the power. It should be noted that although the above-described measurement method is based on the so-called pressurization measurement method, whereby a pulse wave is detected at the time of pressurization of the compressing air bladder 42, the so-called depressurization measurement method, whereby a pulse wave is detected at the time of depressurization of the compressing air bladder 42 may, of course, be employed.

In this embodiment, specifically, the pressurization pump 31 is composed of a piezoelectric pump 100A (see FIG. 4, for example), which will be described below, and the pressurization pump drive circuit 34 is composed of a piezoelectric element drive circuit that controls driving of a piezoelectric element 134 provided in the piezoelectric pump 100A (see FIG. 4, for example). The following is a detailed description of the piezoelectric pump 100A of this embodiment.

Figure 4:
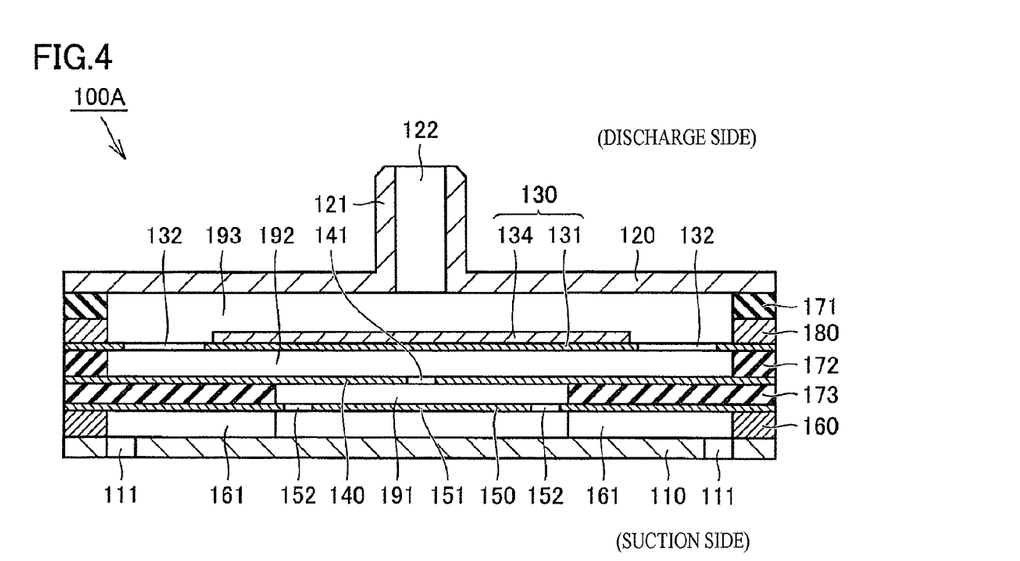
FIG. 4 is a schematic cross-sectional view of the piezoelectric pump of Embodiment 1 of the present invention.
Figure 5:
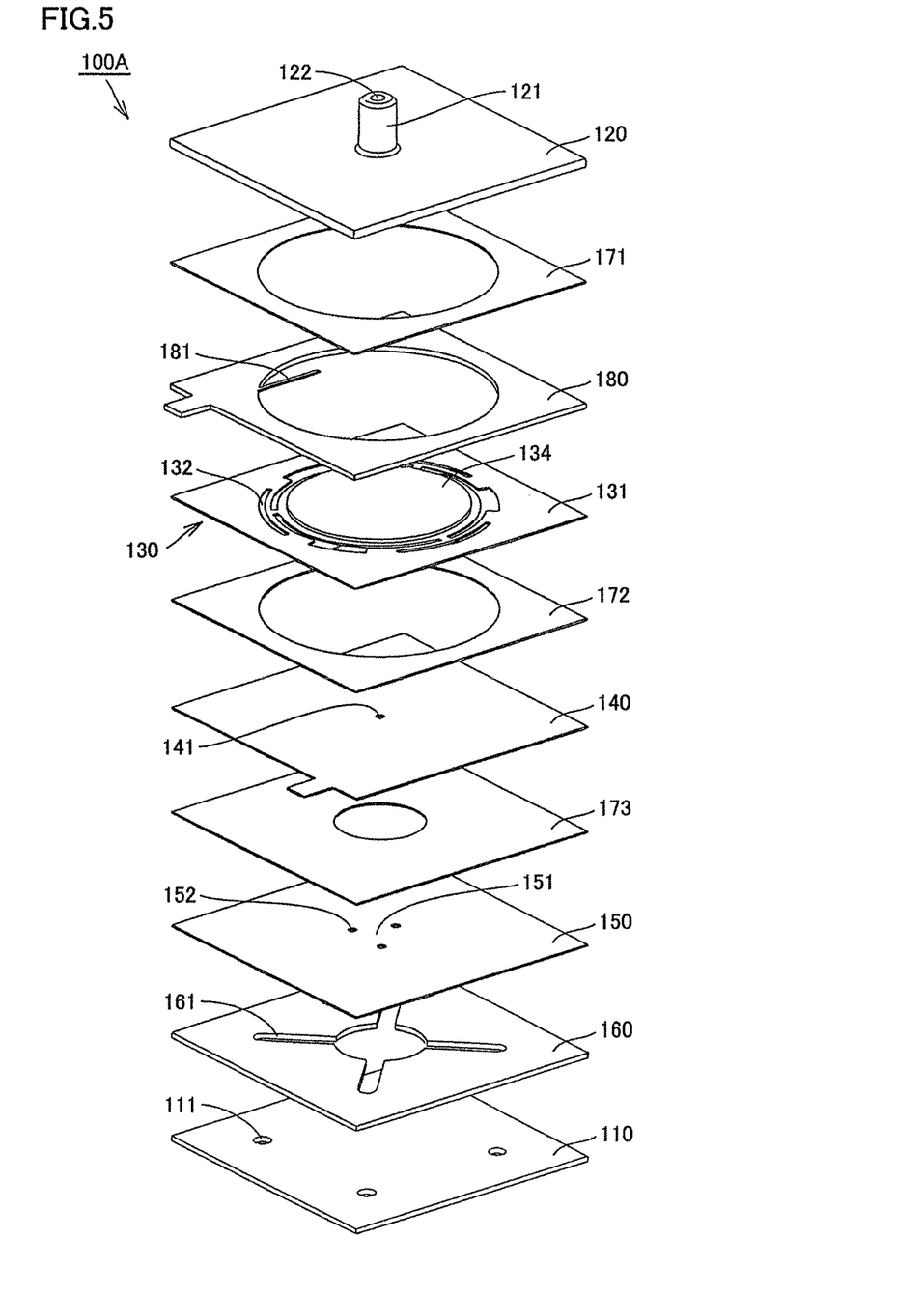
FIG. 5 is a perspective exploded view of the piezoelectric pump of Embodiment 1 of the present invention.

FIG. 4 is a schematic cross-sectional view of the piezoelectric pump of this embodiment, and FIG. 5 is a perspective exploded view of the piezoelectric pump of this embodiment. With reference to FIGS. 4 and 5, the configuration of the piezoelectric pump 100A of this embodiment will be described first.

As shown in FIG. 4, the piezoelectric pump 100A has suction ports 111 provided on the suction side, a discharge port 122 provided on the discharge side, flow channels provided to place the suction port 111 and the discharge port 122 in communication with one another. The piezoelectric pump 100A delivers compressed air by suctioning a fluid, such as air, from the outside into the channels via the suction ports 111 by the operation of a pump chamber 192, which will be described below, and discharging the suctioned air from the flow channel to the outside via the discharge port 122.

As shown in FIGS. 4 and 5, the piezoelectric pump 100A is composed of various thin film and plate components layered and joined together and includes a suction side cover 110, a discharge side cover 120, an actuator 130, a first diaphragm 140, a second diaphragm 150, a suction channel forming plate 160, first to third spacers 171, 172, and 173, and a power supply plate 180.

The suction side cover 110 is composed of a thin metal plate made of, for example, copper, copper alloy, stainless steel, and the like, and has the aforementioned suction ports 111 at predetermined positions close to the outer periphery thereof. The suction side cover 110 is formed to have a thickness of, for example, about 0.5 mm.

The discharge side cover 120 is composed of a thin metal plate made of, for example, stainless steel and the like and has at its central position a tubular discharge portion 121 in which the aforementioned discharge port 122 is provided. The discharge side cover 120 is formed to have a thickness of, for example, about 0.2 mm where the aforementioned discharge portion 121 is not formed.

The actuator 130 is composed of a vibrating sheet 131 and the piezoelectric element 134 attached to the vibrating sheet 131.

The vibrating sheet 131 is composed of a thin metal plate made of, for example, stainless steel and the like and includes a disc-like mount portion located at a central portion to which the piezoelectric element 134 is attached, a plate spring portion surrounding the mount portion, and an outer peripheral portion located outside of the plate spring portion. The plate spring portion is formed by providing cutouts of a predetermined shape in the vibrating sheet 131, and these cutouts provide the vibrating plate 131 with communicating portions 132 in the form of openings. It should be noted that the vibrating sheet 131 also serves as one of the electrodes connected to the piezoelectric element 134. The vibrating sheet 131 is formed to have a thickness of, for example, about 0.2 mm.

The piezoelectric element 134 is made of for example, lead zirconate titanate (PZT), which is highly piezoelectric, and is joined to the aforementioned mount portion of the vibrating sheet 131. The piezoelectric element 134 is formed to have a thickness of, for example, about 0.1 mm.

The first diaphragm 140 is composed of a thin film of phosphor bronze, beryllium bronze, or the like, and has a first connecting hole 141 at the central position thereof. The first diaphragm 140 is formed to have a thickness of, for example, about 0.05 mm to about 0.1 mm.

The second diaphragm 150 is composed of a thin film of phosphor bronze, beryllium bronze, or the like, and has an opposing wall portion 151 at the central position thereof and second connecting holes 152 at predetermined positions closer to the outer periphery in the central portion. In other words, the second connecting holes 152 are provided in a surrounding portion outside of where the opposing wall portion 151 is provided. The second diaphragm 150 is formed to have a thickness of, for example, about 0.05 mm to about 0.1 mm.

The suction channel forming plate 160 is composed of, for example, a thin plate made of phosphor bronze and has an opening of a predetermined shape that defines suction channels 161 in the area that includes the central portion thereof. The suction channel forming plate 160 is formed to have a thickness of, for example, about 0.25 mm.

Each of the first to third spacers 171, 172, and 173 is composed of a thin insulating plate or film and has at its central portion an opening of a predetermined shape that defines the inner space of the piezoelectric pump 100A. The first spacer 171 is composed of a thin plate of glass epoxy and is formed to have a thickness of, for example, about 0.2 mm. The second and third spacers 172 and 173 are composed of a double-faced tape or a coated film formed by applying an epoxy-resin adhesive to a film, and each of the spacers is formed to have a thickness of, for example, about 0.02 mm to 0.05 mm.

The power supply plate 180 is composed of, for example, a thin plate made of phosphor bronze and has at its central portion an opening of a predetermined shape that defines the inner space of the piezoelectric pump 100A and a power supply terminal 181 extending inward within that opening. The power supply terminal 181 serves as the other of the electrodes connected to the piezoelectric element 134. The power supply plate 180 is formed to have a thickness of, for example, about 0.05 mm.

The piezoelectric pump 100A is assembled by layering and joining the aforementioned suction side cover 110, suction channel forming plate 160, second diaphragm 150, third spacer 173, first diaphragm 140, second spacer 172, actuator 130, power supply plate 180, first spacer 171, and discharge side cover 120 in that order.

In this way, in the piezoelectric pump 100A, as shown in FIG. 4, the suction side cover 110, the second diaphragm 150, the first diaphragm 140, the actuator 130, and the discharge side cover 120 are layered in that order from the suction side to the discharge side and spaced apart from one another, such that the suction channels 161, a suction chamber 191, the pump chamber 192, and a discharge chamber 193 to define the aforementioned flow channels are formed between these members.

More particularly, the suction side cover 110 and the second diaphragm 150 are spaced apart by the suction channel forming plate 160, and the suction channels 161 are formed by the space defined by the suction side cover 110, the second diaphragm 150, and the suction channel forming plate 160.

The second diaphragm 150 and the first diaphragm 140 are spaced apart by the third spacer 173, and the suction chamber 191 is formed by the space defined by the second diaphragm 150, the first diaphragm 140, and the third spacer 173.

The first diaphragm 140 and the actuator 130 are spaced apart by the second spacer 172, and the pump chamber 192 is formed by the space defined by the first diaphragm 140, the actuator 130, and the second spacer 172.

The actuator 130 and the discharge side cover 120 are spaced apart by the power supply plate 180 and the first spacer 171, and the discharge chamber 193 is formed by the space defined by the actuator 130, the discharge side cover 120, the power supply plate 180, and the first spacer 171.

Furthermore, the suction channels 161 and the suction chamber 191 are in communication with each other via the second connecting holes 152 provided in the second diaphragm 150, and the suction chamber 191 and the pump chamber 192 are in communication with each other via the first connecting hole 141 provided in the first diaphragm 140. Additionally, the pump chamber 192 and the discharge chamber 193 are in communication with each other via the communicating portions 132 provided in the vibrating sheet 131.

Based on the above, the compressed air delivered by the piezoelectric pump 100A flows from the suction side to the discharge side by way of the suction ports 111, the suction channels 161, the second connecting holes 152, the suction chamber 191, the first connecting hole 141, the pump chamber 192, the communicating portions 132, the discharge chamber 193, and the discharge port 122 in that order.

The first connecting hole 141 provided in the first diaphragm 140 is positioned opposite the central position of the actuator 130. The central position of the actuator 130 is the loop (the point at which the amplitude is the largest) of the actuator 130 when the actuator 130 is vibrated, and the central position of the first diaphragm 140, where the first connecting hole 141 provided, is likewise the loop of the first diaphragm 140 when the first diaphragm 140 is vibrated.

Moreover, the opposing wall portion 151 provided in the second diaphragm 150 is positioned opposite the central position of the first diaphragm 140, where the first connecting hole 141 is provided. As described above, the central position of the first diaphragm 140, where the first connecting hole 141 is provided, becomes the loop of the first diaphragm 140 when the first diaphragm 140 is vibrated, and the central position of the second diaphragm 150, where the opposing wall portion 151 provided, likewise becomes the loop of the second diaphragm 150 when the second diaphragm 150 is vibrated.

Figure 6:
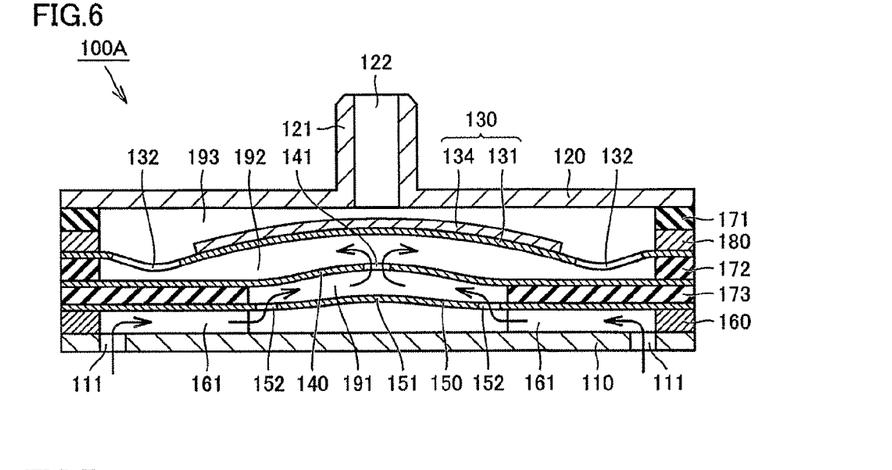
FIG. 6 is a schematic cross-sectional view describing the operation of the piezoelectric pump of Embodiment 1 of the present invention.
Figure 7:
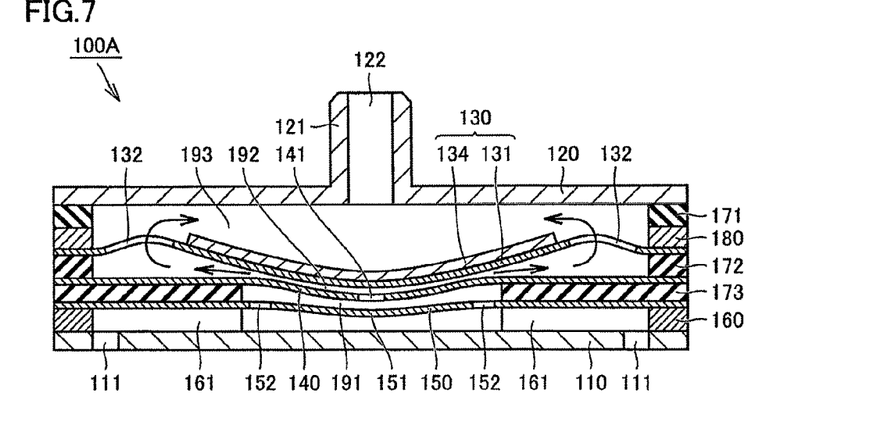
FIG. 7 is a schematic cross-sectional view describing the operation of the piezoelectric pump of Embodiment 1 of the present invention.
Figure 8:
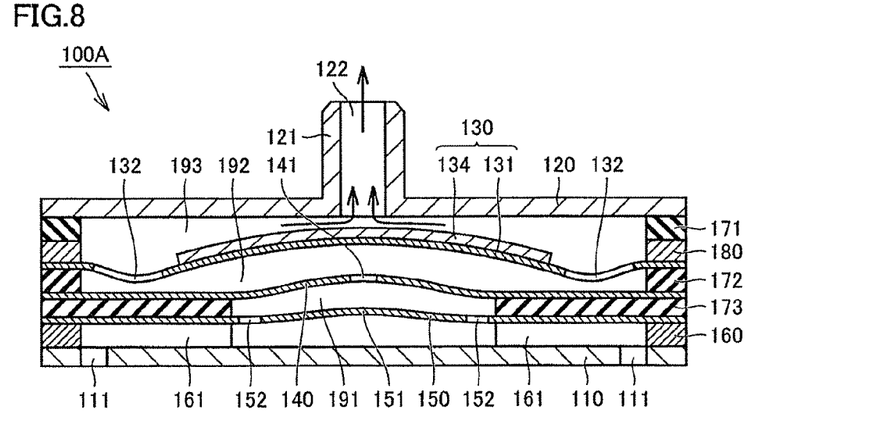
FIG. 8 is a schematic cross-sectional view describing the operation of the piezoelectric pump of Embodiment 1 of the present invention.

FIGS. 6 to 8 are schematic cross-sectional views describing the operation of the piezoelectric pump of this embodiment. With reference to FIGS. 6 to 8, the operation of the piezoelectric pump 100A of this embodiment will be described below.

FIGS. 6 and 8 each show that the actuator 130 is displaced toward the discharge side (i.e., while the pump chamber 192 is performing suction), and FIG. 7 shows that the actuator 130 is displaced toward the suction side (i.e., while the pump chamber 192 is performing discharging). FIGS. 6 and 8 separately show airflows through the flow channels on the suction side and those on the discharge side in different views for ease of understanding. In reality, however, these airflows on the suction side and on the discharge side occur simultaneously.

To drive the piezoelectric pump 100A, an alternating voltage is applied to the piezoelectric element 134. This resonantly drives the piezoelectric element 134 such that the piezoelectric element 134 is alternately deformed into a bulge toward the discharge side and into a bulge toward the suction side as shown in FIGS. 6 to 8. It should be noted that the frequency of the applied alternating voltage is, for example, between about several kHz and tens of kHz, and that the piezoelectric pump is preferably driven at a frequency near the resonance frequency of the entire actuator 130 including the vibrating sheet 131.

As the piezoelectric element 134 deforms, the vibrating sheet 131 also deforms by conforming to that deformation. This results in the actuator 130 vibrating as a whole, such that the actuator 130 vibrates repeatedly between the state in which the actuator is displaced toward the discharge side (i.e., the opposite side to where the first diaphragm 140 is located) and the state in which the actuator 130 is displaced toward the suction side (i.e., the side where the first diaphragm 140 is located).

Due to the aforementioned vibration of the actuator 130, the first diaphragm 140 vibrates in response to the pressure fluctuations of the pump chamber 192. In other words, the first diaphragm 140 repeatedly vibrates between the state in which the first diaphragm 140 is displaced toward the discharge side and the state in which the first diaphragm 140 is displaced toward the suction side. During that process, as the vibration of the first diaphragm 140 is caused by the aforementioned pressure fluctuations of the pump chamber 192, the first diaphragm 140 vibrates with a slight phase delay (i.e., phase difference) relative to the vibration of the actuator 130.

Due to the aforementioned vibration of the first diaphragm 140, the second diaphragm 150 vibrates in response to the pressure fluctuations of the suction chamber 191. In other words, the second diaphragm 150 repeatedly vibrates between the state in which the second diaphragm 150 is displaced toward the discharge side and the state in which the second diaphragm 150 is displaced toward the suction side. During that process, as the vibration of the second diaphragm 150 is caused by the aforementioned pressure fluctuations of the suction chamber 191, the second diaphragm 150 vibrates with a slight phase delay (i.e., phase difference) relative to the vibration of the first diaphragm 140.

Due to the above, the volume fluctuations occur in the pump chamber 192 as a result of the displacement of the actuator 130 and the first diaphragm 140, and the volume fluctuations in the pump chamber 192 translate to a driving force to cause the pump chamber 192 to perform a pumping operation.

Specifically, as shown in FIG. 6, as the actuator 130 is displaced toward the discharge side, the volume of the pump chamber 192 increases, and as this in turn reduces the internal pressure of the pump chamber 192, a negative pressure is created. This causes air from the outside to be introduced into the pump chamber 192 via the suction ports 111, the suction channels 161, the second connecting holes 152, the suction chamber 191, and the first connecting hole 141.

Next, as shown in FIG. 7, as the actuator 130 is displaced toward the suction side, the volume of the pump chamber 192 decreases, and as this in turn increases the internal pressure of the pump chamber 192, a positive pressure is created. This causes the air in the pump chamber 192 to move outward in the pump chamber 192 and be delivered into the discharge chamber 193 via the communicating portions 132.

Next, as shown in FIG. 8, as the actuator 130 is displaced again toward the discharge side, the volume of the discharge chamber 193 decreases, and as this in turn increases the internal pressure of the discharge chamber 193, a positive pressure is created. This causes the air in the discharge chamber 193 to be discharged to the outside via the discharge port 122.

During this process, as described above, in the state of the actuator 130 in which it is displaced toward the suction side as shown in FIG. 7, part of the air in the pump chamber 192 would flow back to the suction side via the first connecting hole 141 provided in the first diaphragm 140 (air leakage), which could be an obstacle to obtain a higher pressurization capability.

According to the piezoelectric pump 100A of this embodiment, however, as the second diaphragm 150, which has the opposing wall portion 151 in the portion thereof that opposes the first connecting hole 141, is provided, the opposing wall portion 151 serves as a backflow preventing portion that effectively prevents the occurrence of the aforementioned backflow.

In other words, in the state shown in FIG. 7, the first diaphragm 140 and the second diaphragm 150 are both displaced toward the suction side. Based on the aforementioned phase difference, the distance is narrowed between the part of the first diaphragm 140 in which the first connecting hole 141 is provided and the part of the second diaphragm 150 in which the opposing wall portion 151 is provided. For that reason, the flow resistance increases in this region due to the viscosity of air, thus allowing the opposing wall portion 151 to serve, in a sense, as a throttle valve for the first connecting hole 141.

Accordingly, air is prevented from flowing back from the pump chamber 192 toward the suction side, thereby enhancing the pressurization capability.

Unlike the foregoing structure, it is also possible to position the suction side cover 110 as close as possible to the first diaphragm 140 while eliminating the second diaphragm 150 such that, in the state in which the actuator 130 is displaced toward the suction side, backflow may be prevented due to an increased flow resistance in the region between the part of the first diaphragm 140 in which the first connecting hole 141 is provided and the suction side cover 110.

If that structure is employed, however, the flow resistance in that region will remain high immediately after the first diaphragm 140 has started to be displaced toward the discharge side from the state in which it is maximally displaced toward the suction side (i.e., immediately after the pump chamber 192 has switched over from discharge operation to suction operation). Accordingly, the high flow resistance adversely lowers the suction capability, thus resulting in a decreased pressurization capability.

Conversely, in the piezoelectric pump 100A of this embodiment, immediately after the first diaphragm 140 has started to be displaced toward the discharge side from the state in which it is maximally displaced toward the suction side, based on the aforementioned phase difference, the distance sharply increases between the part of the first diaphragm 140 in which the first connecting hole 141 is provided and the part of the second diaphragm 150 in which the opposing wall portion 151 is provided. This sharply increases the flow resistance in the region so as not to reduce the suction capability. Rather, combined with the above-described prevention of backflow, this greatly enhances the pressurization capacity.

As described above, according to the piezoelectric pump 100A of this embodiment, the situation in which part of the air in the pump chamber 192 flows back toward the suction side can be prevented, thus providing a high-pressure, large-flow piezoelectric pump with a superior pressurization efficiency. Therefore, according to the blood pressure monitor 1 of this embodiment, insufficient pressure force does not occur in the compressing air bladder 42 and measurement is possible in a short period of time.

It should be noted that preferably, the second diaphragm 150 is composed of a component more difficult to deflect than the first diaphragm 140. In this way, in the state in which the first diaphragm 140 is maximally displaced toward the suction side, the distance is further narrowed between the part of the first diaphragm 140 in which the first connecting hole 141 is provided and the part of the second diaphragm 150 in which the opposing wall portion 151 is provided.

Accordingly, if this structure is employed, air is more effectively prevented from flowing back from the pump chamber 192 toward the suction side, thus further enhancing the pressurization capability. It should be noted that in order to make the second diaphragm 150 more difficult to deflect than the first diaphragm 140, the material, thickness, or the like thereof may be adjusted as required.

Embodiment 2

Figure 9:
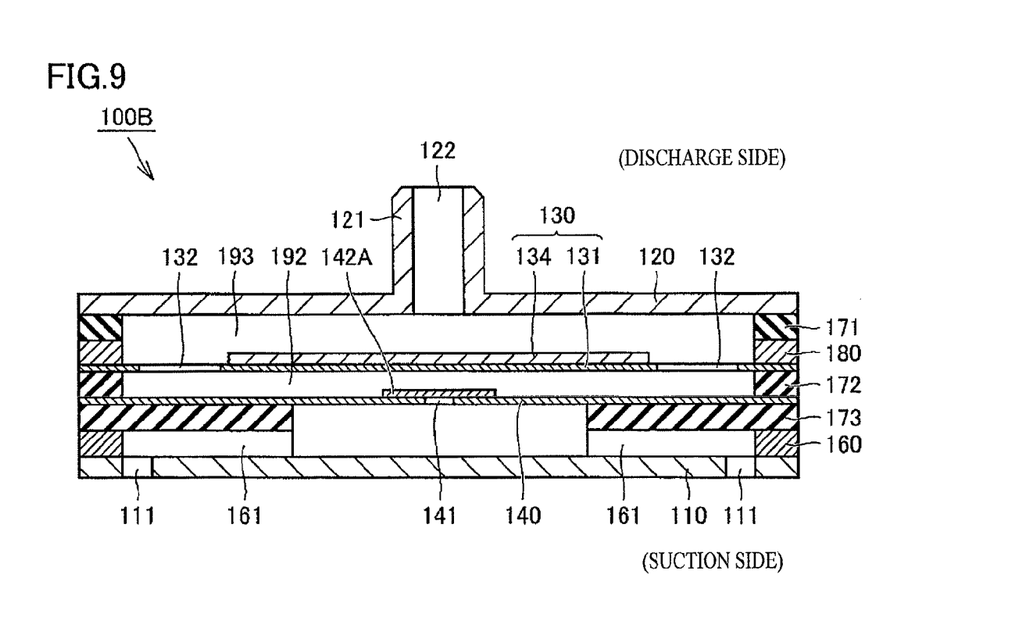
FIG. 9 is a schematic cross-sectional view of the piezoelectric pump of Embodiment 2 of the present invention.
Figure 10:
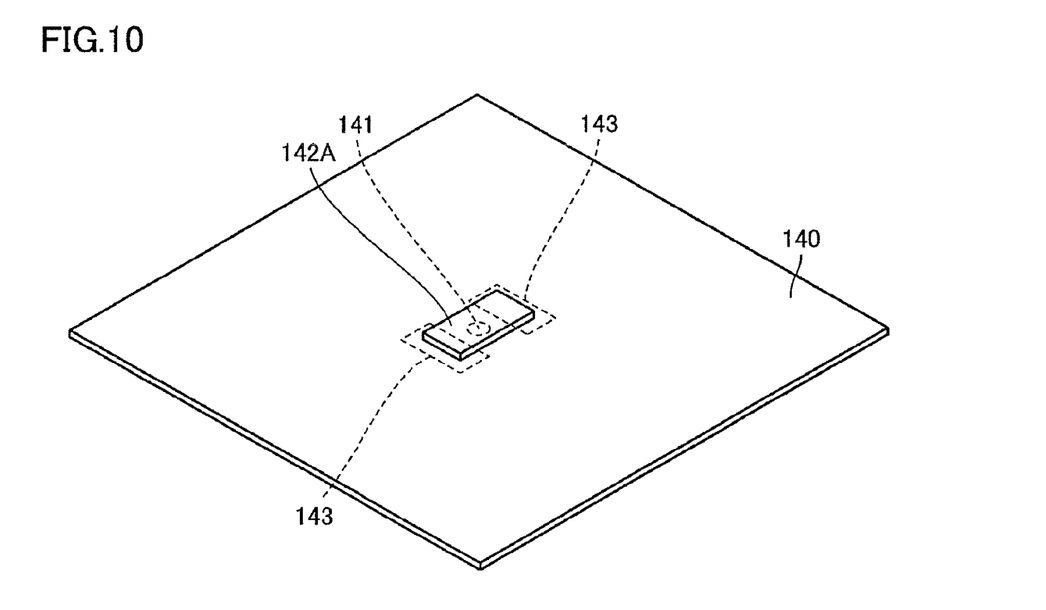
FIG. 10 is a perspective view of a first diaphragm of the piezoelectric pump of Embodiment 2 of the present invention.

FIG. 9 is a schematic cross-sectional view of a piezoelectric pump of Embodiment 2 of the present invention, and FIG. 10 is a perspective view of a first diaphragm of the piezoelectric pump of this embodiment. With reference to FIGS. 9 and 10, the configuration of the piezoelectric pump 100B of this embodiment will be described first. It should be noted that as in the case of the foregoing Embodiment 1, the piezoelectric pump 100B of this embodiment is also provided in the blood pressure monitor 1 as the pressurization pump 31 for pressurizing the compressing air bladder 42.

As shown in FIG. 9, compared with the piezoelectric pump 100A of the foregoing Embodiment 1, the piezoelectric pump 100B differs in that it does not include a second diaphragm 150 but has a thin-film valve body 142A as a backflow preventing portion in place of the opposing wall portion 151 provided in the second diaphragm 150.

As shown in FIGS. 9 and 10, the valve body 142A is attached to the portion of the first diaphragm 140 facing the actuator 130 in a manner that covers the first connecting hole 141. As shown in FIG. 10, the valve body 142A is joined to the first diaphragm 140 in joining portions 143, which constitute part of the periphery of the valve body 142A, for example, with an adhesive or the like, and the remaining portions of the periphery are not joined to the first diaphragm 140. The valve body 142A is capable of blocking and opening the first connecting hole 141 to serve as a check valve.

Figure 11:
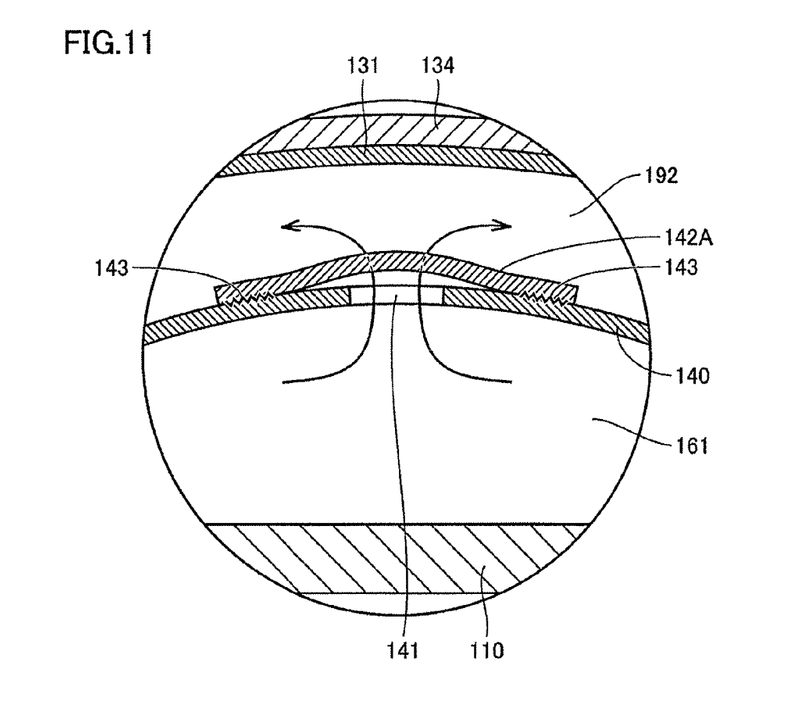
FIG. 11 is an enlarged schematic cross-sectional view describing the operation of the piezoelectric pump of Embodiment 2 of the present invention.
Figure 12:
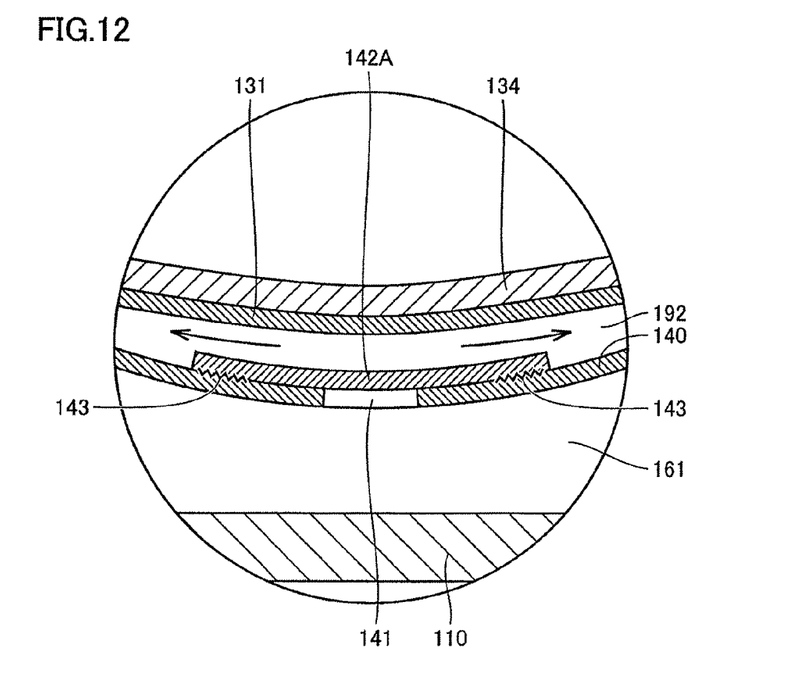
FIG. 12 is an enlarged schematic cross-sectional view describing the operation of the piezoelectric pump of Embodiment 2 of the present invention.

FIGS. 11 and 12 are enlarged schematic cross-sectional views describing the operation of the piezoelectric pump of this embodiment. With reference to FIGS. 11 and 12, the operation of the piezoelectric pump 100B of this embodiment will be described below.

As shown in FIGS. 11 and 12, also in the piezoelectric pump 100B of this embodiment as in the foregoing Embodiment 1, as the actuator 130 vibrates, the first diaphragm 140 repeatedly vibrates between the state in which the first diaphragm 140 is displaced toward the discharge side and the state in which the first diaphragm 140 is displaced toward the suction side.

As shown in FIG. 11, when the first diaphragm 140 is displaced toward the discharge side, negative pressure is created due to the deformation of the first diaphragm 140 and the increase in the volume of the pump chamber 192, thus deforming the valve body 142A into a bulge toward the discharge side. This creates a gap between the aforementioned non-joined portions of the valve body 142A and the first diaphragm 140, thus introducing air into the pump chamber 192 via the gap and the first connecting hole 141.

On the other hand, as shown in FIG. 12, when the first diaphragm 140 is displaced toward the suction side, positive pressure is created due to the deformation of the first diaphragm 140 and the decrease in the volume of the pump chamber 192, such that the valve body 142A is pressed against the first diaphragm 140. As this brings the valve body 142A into close contact with the first diaphragm 140, the aforementioned gap is closed to prevent backflow of air from the pump chamber 192 toward the suction side (air leakage).

Therefore, according to the piezoelectric pump 100B of this embodiment, as in the case of the foregoing Embodiment 1, the situation in which part of the air in the pump chamber 192 flows back toward the suction side can be prevented, thus providing a high-pressure, large-flow piezoelectric pump with a superior pressurization efficiency.

Figure 13:
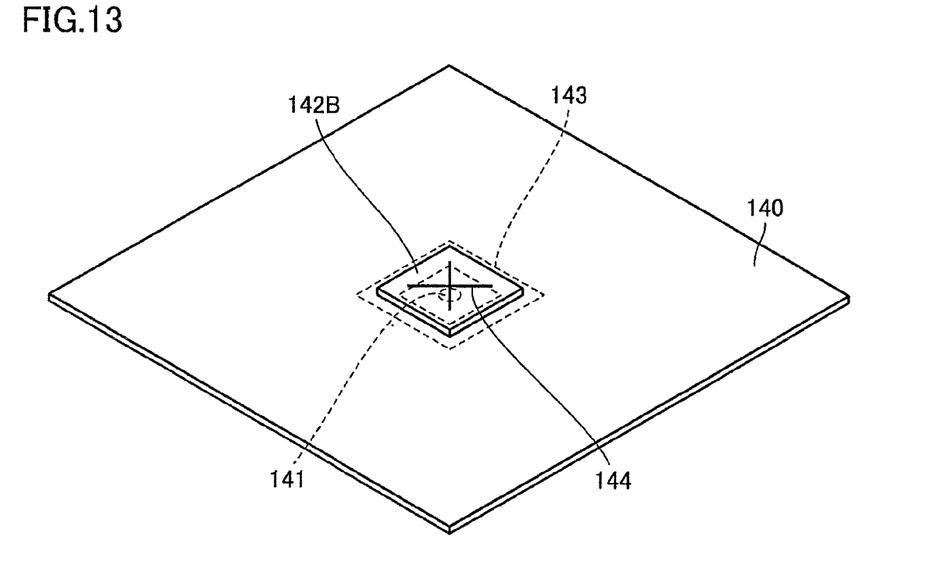
FIG. 13 is a perspective view of a first diaphragm of a variant piezoelectric pump based on Embodiment 2 of the present invention.
Figure 14:
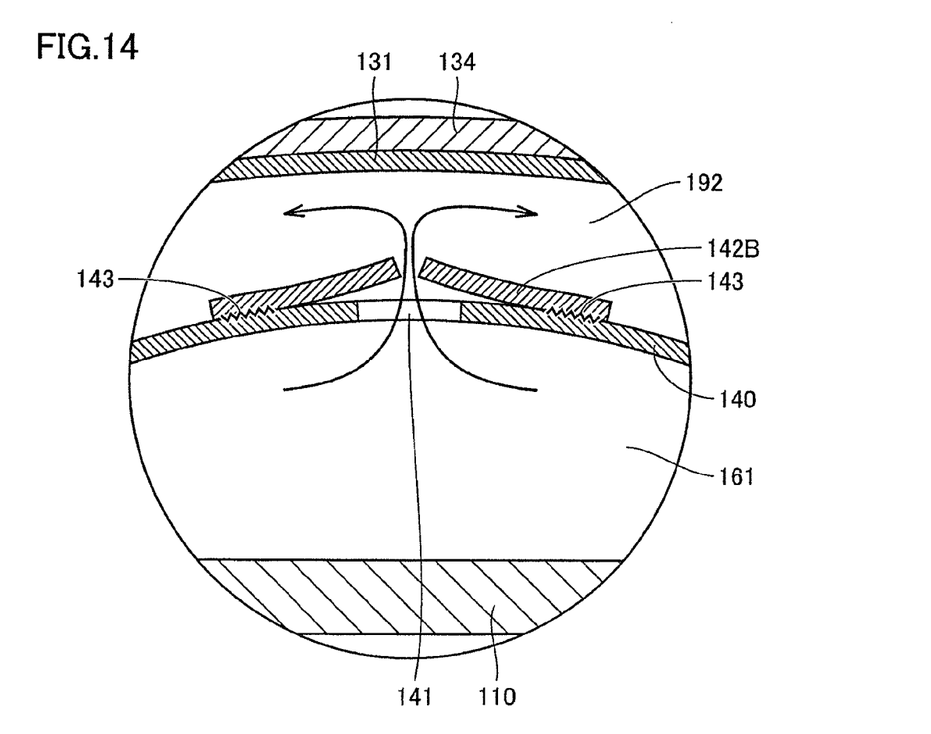
FIG. 14 is an enlarged schematic cross-sectional view describing the operation of the variant piezoelectric pump based on Embodiment 2 of the present invention.
Figure 15:
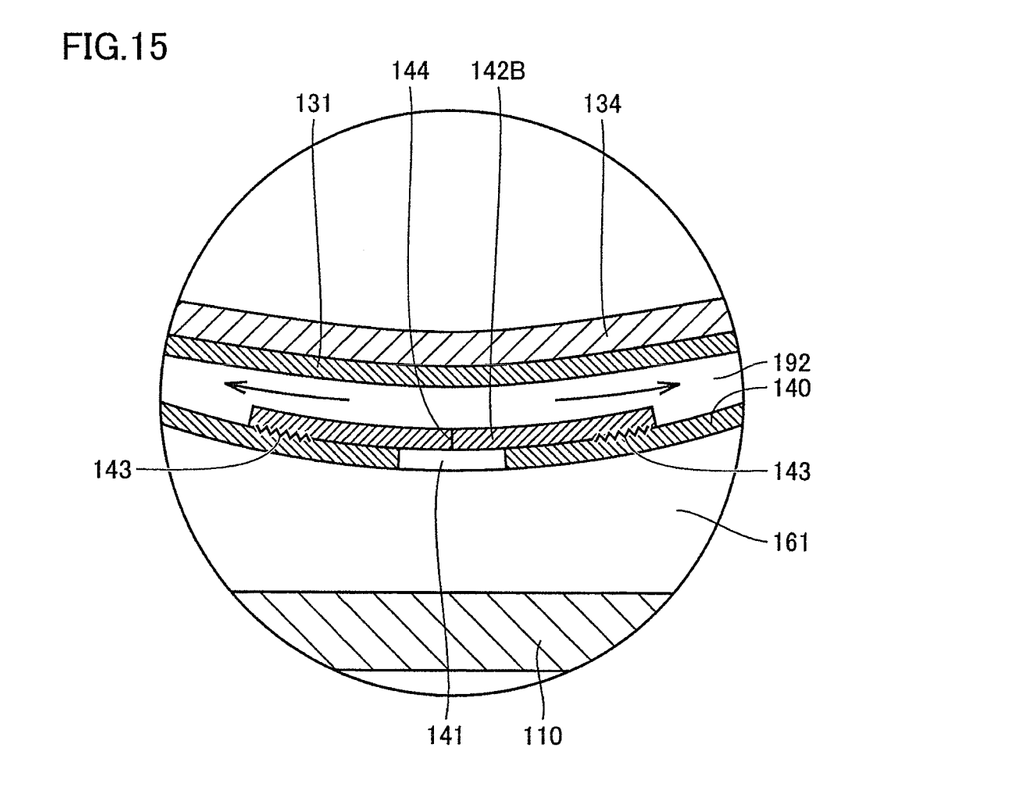
FIG. 15 is an enlarged schematic cross-sectional view describing the operation of the variant piezoelectric pump based on Embodiment 2 of the present invention.

FIG. 13 is a perspective view of a first diaphragm of a variant piezoelectric pump based on this embodiment, and FIGS. 14 and 15 are enlarged schematic cross-sectional views illustrating the operation of this variant piezoelectric pump. With reference to FIGS. 13 to 15, this variant piezoelectric pump will be described hereinafter.

As shown in FIGS. 13 to 15, the variant piezoelectric pump is provided with a valve body 142B having a different configuration from that of the foregoing piezoelectric pump 100B of the embodiment. The valve body 142B is attached to the portion of the first diaphragm 140 facing the actuator 130 in a manner that covers the first connecting hole 141, and the valve body 142B has an X-shaped slit 144 at a predetermined position. Furthermore, the valve body 142B is joined to the first diaphragm 140 in the joining portion 143 provided all around the valve body 142B, for example, with an adhesive or the like. The valve body 142B is capable of blocking and opening the first connecting hole 141 to serve as a check valve.

As shown in FIG. 14, when the first diaphragm 140 is displaced toward the discharge side, negative pressure is created due to the deformation of the first diaphragm 140 and the increase in the volume of the pump chamber 192, thus deforming the valve body 142B into a bulge toward the discharge side. This creates a gap in the portion of the valve body 142B in which the aforementioned slit 144 is provided, thus introducing air into the pump chamber 192 via the gap and the first connecting hole 141.

On the other hand, as shown in FIG. 15, when the first diaphragm 140 is displaced toward the suction side, positive pressure is created due to the deformation of the first diaphragm 140 and the decrease in the volume of the pump chamber 192, such that the valve body 142B is pressed against the first diaphragm 140. As this brings the valve body 142B into close contact with the first diaphragm 140, the aforementioned gap is closed to prevent backflow of air from the pump chamber 192 toward the suction side.

Accordingly, the configuration of this variant can also provide the same effect as the foregoing configuration of the embodiment. It should be noted that in addition to the aforementioned X-shape, the slit 144 provided in the valve body 142B may have an I-, H-, U-shape, or the like.

In the foregoing embodiments of the present invention and the variants thereof, piezoelectric pumps with a piezoelectric element attached to the discharge-side main surface of a vibrating sheet have been described as examples. However, it is of course possible to attach a piezoelectric element to the suction-side main surface of the vibrating sheet.

Moreover, in the foregoing embodiments of the present invention and the variants thereof, cases where suction ports and a discharge port are provided on the top surface and the bottom surface of the piezoelectric pump, which are located in the directions of the normal to the main surfaces of the actuator, have been described as examples. However, the locations of these suction and discharge ports are not so limited, but one or both types of ports may be provided on the peripheral surface of the piezoelectric pump, or both may be provided on one of the foregoing top and bottom surfaces.

Moreover, in the foregoing embodiments of the present invention and the variants thereof, cases where the compressed fluid for delivery is air have been described as examples. However, the applicability of the present invention is not so limited; the compressed fluid for delivery may be a gas other than air or a liquid.

Furthermore, the characteristic configurations shown in the foregoing embodiments of the present invention and the variants thereof may naturally be combined with one another as required.

Furthermore, in the foregoing embodiments of the invention and the variants thereof, an upper arm blood pressure monitor for measuring blood pressure values such as a systolic blood pressure value and a diastolic blood pressure value has been described as an example of the blood pressure information measurement device. However, it goes without saying that the invention can also be applied to a wrist blood pressure monitor, a leg blood pressure monitor, and a blood pressure information measurement device that enables measurement of the pulse wave or the pulse, an index indicating the level of arteriosclerosis, which is typified by the AI (Augmentation Index) value, an average blood pressure value, oxygen saturation, and the like.

In this manner, the embodiments and variants thereof disclosed herein are to be considered in all respects as illustrative and not restrictive. The technical scope of the present invention is defined by the appended claims and intended to encompass equivalents to the claims and all changes that fall within the scope of the claims.

REFERENCE SIGNS LIST

1 blood pressure monitor
10 main body
20 control unit
21 display unit
22 memory unit
23 operation unit
24 power supply unit
30 compressing air system components
31 pressurization pump
32 exhaust valve
33 pressure sensor
34 pressurization pump drive circuit
35 exhaust valve drive circuit
36 oscillation circuit
40 cuff
41 outer package cover
42 compressing air bladder
50 air tube
100A, 100B piezoelectric pump
110 suction side cover 111 suction ports
120 discharge side cover
121 discharge portion
122 discharge port
130 actuator
131 vibrating sheet
132 communicating portions
134 piezoelectric element
140 first diaphragm
141 first connecting hole
142A, 142B valve body
143 joining portions
144 slit
150 second diaphragm
151 opposing wall portion
152 second connecting holes
160 suction channel forming plate
161 suction channels
171 first spacer
172 second spacer
173 third spacer
180 power supply plate
181 power supply terminal
191 suction chamber
192 pump chamber
193 discharge chamber

The invention claimed is:

1. A piezoelectric pump for suctioning a fluid from a suction port of the pump and discharging the suctioned fluid through a discharge port, the piezoelectric pump comprising:
   an actuator including a piezoelectric element and a vibrating sheet to which the piezoelectric element is attached, wherein the actuator is vibrated by the piezoelectric element being resonantly driven;
   a discharge chamber formed on one side of the vibrating sheet, said discharge chamber formed with the discharge port;
   a first diaphragm having therein a first connecting hole through which the fluid flows, wherein the first diaphragm is vibrated with the vibration of the actuator by being positioned on the opposite side of the vibrating sheet;
   a second diaphragm that is vibrated with the vibration of the first diaphragm by being on the opposite side of the first diaphragm from the actuator and positioned opposite the first diaphragm, the second diaphragm having a second connecting hole through which the fluid flows;
   a pump chamber facing the discharge chamber and formed within a space between the actuator and the first diaphragm on said opposite side of the vibrating sheet, wherein
      the pump chamber introduces the fluid thereinto from the suction port positioned on said opposite side of the vibrating sheet via the first connecting hole by the actuator being displaced toward a side opposite to where the first diaphragm is located, and
      the pump chamber delivers the fluid to the discharge chamber by the actuator being displaced toward the side where the first diaphragm is located; and
   a backflow preventing portion that prevents the fluid introduced into the pump chamber via the first connecting hole from flowing back toward the suction port via the first connecting hole, wherein the backflow preventing portion is composed of an opposing wall portion provided in a portion of the second diaphragm that opposes the first connecting hole.

2. A piezoelectric pump according to claim 1, wherein the second diaphragm is composed of a component more difficult to deflect than the first diaphragm.

3. A piezoelectric pump according to claim 1, wherein a second connecting hole through which the fluid flows is provided in a surrounding portion outside of where the opposing wall portion of the second diaphragm is provided, and wherein the fluid is introduced into the pump chamber from the suction port via the second connecting hole and the first connecting hole by displacement of the actuator toward the opposite side to where the first diaphragm is located.

4. A piezoelectric pump according to claim 1, comprising a thin-film valve body attached to a portion of the first diaphragm facing the actuator in a manner that covers the first connecting hole, wherein
   the valve body is capable of blocking or opening the first connecting hole, and
   the backflow preventing portion is composed of the valve body.

5. A piezoelectric pump according to claim 4, wherein the valve body functions as a check valve with part of the periphery thereof not joined to the first diaphragm.

6. A piezoelectric pump according to claim 4, wherein the valve body functions as a check valve by having a slit formed in a portion thereof.

7. A blood pressure information measurement device comprising the piezoelectric pump of claim 1 as a pressure pump that pressurizes a compressing fluid bladder for compressing a living body.

8. A piezoelectric pump according to claim 2, wherein
   a second connecting hole through which the fluid flows is provided in a surrounding portion outside of where the opposing wall portion of the second diaphragm is provided, and
   the fluid is introduced into the pump chamber from the suction port via the second connecting hole and the first connecting hole by displacement of the actuator toward the opposite side to where the first diaphragm is located.

9. A blood pressure information measurement device comprising the piezoelectric pump of claim 2 as a pressure pump that pressurizes a compressing fluid bladder for compressing a living body.

10. A blood pressure information measurement device comprising the piezoelectric pump of claim 3 as a pressure pump that pressurizes a compressing fluid bladder for compressing a living body.

11. A blood pressure information measurement device comprising the piezoelectric pump of claim 4 as a pressure pump that pressurizes a compressing fluid bladder for compressing a living body.

12. A blood pressure information measurement device comprising the piezoelectric pump of claim 5 as a pressure pump that pressurizes a compressing fluid bladder for compressing a living body.

13. A blood pressure information measurement device comprising the piezoelectric pump of claim 6 as a pressure pump that pressurizes a compressing fluid bladder for compressing a living body.

14. A blood pressure information measurement device comprising the piezoelectric pump of claim 8 as a pressure pump that pressurizes a compressing fluid bladder for compressing a living body.

15. A piezoelectric pump according to claim 1, wherein the vibrating sheet has a hole formed thereon that connects the pump chamber and the discharge chamber.

* * * * *